United States Patent [19]
Jost et al.

[11] Patent Number: 4,914,211
[45] Date of Patent: Apr. 3, 1990

[54] PIGMENT COMPOSITIONS

[75] Inventors: Max Jost, Oberwil; Abul Iqbal, Ettingen; Alain C. Rochat, Fribourg, all of Switzerland

[73] Assignee: Ciba-Geigy Corporation, Ardsley, N.Y.

[21] Appl. No.: 231,324

[22] Filed: Aug. 12, 1988

Related U.S. Application Data

[62] Division of Ser. No. 932,258, Nov. 19, 1986, Pat. No. 4,791,204.

[30] Foreign Application Priority Data

Nov. 26, 1985 [CH] Switzerland ........................ 5054/85

[51] Int. Cl.[4] .................. C07D 498/04; C07D 401/14; C07D 403/14

[52] U.S. Cl. .................................... 548/453; 546/199; 544/144

[58] Field of Search ......................... 548/453; 546/199; 544/144

[56] References Cited

U.S. PATENT DOCUMENTS

| | | |
|---|---|---|
| 4,256,507 | 3/1981 | Kranz et al. . |
| 4,334,932 | 6/1982 | Roueche . |
| 4,415,685 | 11/1983 | Iqbal et al. . |
| 4,490,542 | 12/1984 | Iqbal et al. . |
| 4,540,791 | 9/1985 | Cassar et al. . |
| 4,579,949 | 4/1986 | Rochat et al. . |
| 4,585,878 | 4/1986 | Jost et al. . |
| 4,613,669 | 9/1986 | Cassar et al. . |
| 4,659,775 | 4/1987 | Pfenninger et al. . |
| 4,720,305 | 1/1988 | Iqbal et al. . |
| 4,778,899 | 10/1988 | Pfenninger et al. . |

*Primary Examiner*—David B. Springer
*Attorney, Agent, or Firm*—Luther A. R. Hall

[57] ABSTRACT

Compositions comprising (a) a pyrrolopyrrole of formula I

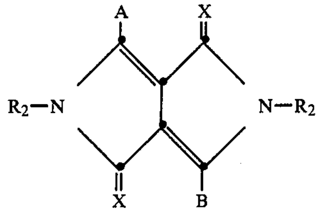

(I)

wherein A and B are identical or different alkyl, arlkyl, aryl or heterocyclic aromatic radicals, $R_1$ and $R_2$ are hydrogen atoms, unsubstituted or substituted alkyl radicals, and also alkenyl, alkynyl, aralkyl, cycloalkyl, carbamoyl, alkylcarbamoyl, arylcarbamoyl, alkoxycarbonyl, aryl, alkanoyl or aroyl groups, and X is an —O— or —S— atom, and (b) a pyrrolopyrrole of the above formula I that contains at least one group of formula $—SO_3L$, $—CO_2L$, $—PO_3(L)_2$, $—N(R_4)(R_5)$,

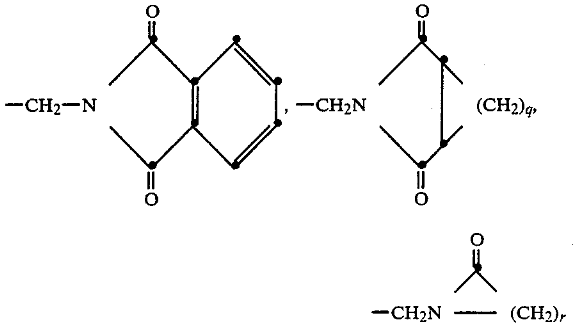

or —NHCOR wherein L is —H, a group of formula $$\frac{M^{+n}}{n}$$

or $N^+H(R_3)(R_4)(R_5)$, M is monovalent, divalent or trivalent metal cation, n is 1, 2 or 3, $R_3$, $R_4$ and $R_5$ are each independently —H or alkyl, aralkyl, $C_5$-$C_6$cycloalkyl or aryl radicals, or $R_4$ and $R_5$, together with the nitrogen atom to which they are attached, form a 5— or 6-membered heterocyclic radical, q is an integer from 0 to 4, r is an integer from 3 to 5 and R is aryl or $C_1$-$C_4$alkyl, are suitable for coloring high molecular organic material.

5 Claims, No Drawings

PIGMENT COMPOSITIONS

This is a divisional of application Ser. No. 932,258, filed on November 19, 1986, now U.S. Pat. No. 4,791,204, issued on December 13, 1988.

The present invention relates to novel compositions based on pyrrolopyrroles, to a process for their preparation, and to the use thereof for colouring high molecular organic material.

Diketopyrrolopyrroles are known compounds which have been described as pigments for colouring organic polymers in e.g. U.S. Pat. No. 4,415,685 or European published patent application No. 0,133,156. Some of their pigment properties are not satisfactory in all respects. It has now been found that an unexpected enhancement of certain pigment properties can be achieved by introducing selected groups into the molecule of these compounds.

Accordingly, the present invention relates to compositions comprising (a) a pyrrolopyrrole of formula I

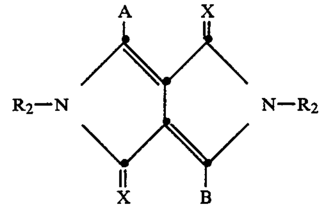
(I)

wherein A and B are identical or different alkyl, aralkyl, aryl or heterocyclic aromatic radicals, $R_1$ and $R_2$ are hydrogen atoms, unsubstituted or substituted alkyl radicals, and also alkenyl, alkynyl, aralkyl, cycloalkyl, carbamoyl, alkylcarbamoyl, arylcarbamoyl, alkoxycarbonyl, aryl, alkanoyl or aroyl groups, and X is an —O— or —S— atom, and (b) a pyrrolopyrrole of the above formula I that contains at least one group of formula $—SO_3L$, $—CO_2L$, $—PO_3(L)_2$, $—N(R_4)(R_5)$,

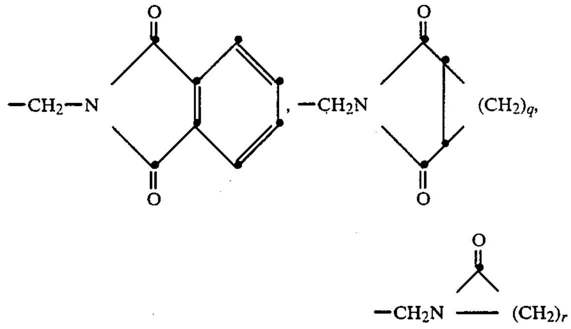

or —NHCOR wherein L is —H, a group of formula $$\frac{M^{+n}}{n}$$

or $N^+H(R_3)(R_4)(R_5)$, M is a monovalent, divalent or trivalent metal cation, n is 1, 2 or 3, $R_3$, $R_4$ and $R_5$ are each independently —H or alkyl, aralkyl, $C_5$–$C_6$cycloalkyl or aryl radicals, or $R_4$ and $R_5$, together with the nitrogen atom to which they are attached, form a 5- or 6-membered heterocyclic radical, q is an integer from 0 to 4, r is an integer from 3 to 5 and R is aryl or $C_1$–$C_4$alkyl.

The radicals A and B are preferably identical and the preferred meaning is aryl.

Unsubstituted alkyl groups A, B, $R_1$ and $R_2$ may be branched or unbranched and preferably contain 1 to 18, in particular 1 to 12 and, most preferably, 1 to 6, carbon atoms. Examples of such groups are: methyl, ethyl, isopropyl, sec-butyl, tert-butyl, tert-amyl, octyl, decyl, dodecyl and stearyl.

Substituted alkyl groups $R_1$ and $R_2$ may be branched or unbranched and preferably contain 1 to 18, in particular 1 to 12 and, most preferably, 1 to 6, carbon atoms, and carry water-insolubilising substituents. Examples of such substituents are: fluorine, chlorine, cyano, $C_1$–$C_6$alkoxy, phenoxy or phenoxy which is substituted by chlorine, $C_1$–$C_4$alkyl or $C_1$–$C_4$alkoxy, naphthoxy, $C_2$–$C_6$carbalkoxy or heterocyclic aromatic radicals such as 2-thienyl, 2-benzoxazolyl, 2-benzimidazolyl, 2-, 3- or 4-pyridyl, 2-, 4- or 6-quinolyl. Examples of substituted alkyl groups are trifluoromethyl, trifluoroethyl, cyanomethyl or methoxycarbonylmethyl.

Alkenyl and alkynyl groups may be branched or unbranched and contain preferably 2 to 18, most preferably 2 to 6, carbon atoms. Examples of alkenyl and alkynyl groups are: ethenyl, propenyl, butenyl, isobutenyl, isopropenyl, 1-pentenyl, 2-methyl-2-butenyl, 3-methyl-1-butenyl, 3-propyl-1-hexenyl, propadienyl, 1,2-butadienyl, ethynyl, propargyl, 1-butynyl or 4-methyl-2-pentynyl.

R as $C_1$–$C_4$alkyl is e.g. methyl, ethyl, n-propyl or n-butyl.

A, B, $R_1$ and $R_2$ as aryl groups are e.g. mono- to tetracyclic radicals, preferably mono- or bicyclic radicals, e.g. phenyl, 4-biphenylyl or naphthyl, but are most preferably phenyl or phenyl which is substituted by water-insolubilising substituents. Examples of water-insolubilising substituents are: halogen such as chlorine, bromine and fluorine, $C_1$–$C_6$alkyl such as methyl, ethyl, isopropyl or tert-butyl, $C_1$–$C_6$alkoxy such as methoxy or ethoxy, $C_1$–$C_6$alkylmercapto such as methylmercapto, trifluoromethyl, cyano, dimethylamino, diethylamino, $C_2$–$C_6$alkoxycarbonyl such as methoxycarbonyl or ethoxycarbonyl, acetylamino, carbamoyl or sulfamoyl.

R as aryl is e.g. a phenyl or naphthyl group which is unsubstituted or substituted by the water-insolubilising substituents cited above.

A, B, $R_1$, $R_2$, $R_3$, $R_4$ and $R_5$ as aralkyl groups are preferably those containing a branched or unbranched alkyl chain which contains 1 to 12, preferably 1 to 6 and, most preferably, 1 to 4, carbon atoms and a preferably mono- or bicyclic aryl radical. Typical examples are benzyl and phenylethyl.

$R_1$ and $R_2$ as cycloalkyl are e.g. cyclopentyl or cyclohexyl.

A and B as heterocyclic aromatic radicals are preferably mono- to tricyclic radicals. These radicals may be purely heterocyclic or contain a heterocyclic ring and one or more fused benzene rings, e.g. pyridyl, pyrimidyl, pyrazinyl, triazinyl, furyl, pyrrolyl, thienyl, quinolyl, coumarinyl, benzfuranyl, benzimidazolyl or benzoxazolyl. The heterocyclic aromatic radicals may contain customary substituents, for example those cited in European patent specification No. 0,061,426.

$R_1$ and $R_2$ as alkylcarbamoyl may be branched or unbranched alkylcarbamoyl, the alkyl moiety of which contains 1 to 18, preferably 1 to 12, in particular 1 to 8 and, most preferably, 1 to 4, carbon atoms. Typical examples are: N-methylcarbamoyl, N-ethylcarbamoyl and N,N-dimethylcarbamoyl.

$R_1$ and $R_2$ as arylcarbamoyl are e.g. N-phenylcarbamoyl and N-α-naphthylcarbamoyl.

$R_1$ and $R_2$ as alkoxycarbonyl are preferably $C_2$–$C_{13}$alkoxycarbonyl groups, e.g. methoxycarbonyl, ethoxycarbonyl, n-propoxycarbonyl, n-butoxycarbonyl and n-hexyloxycarbonyl.

$R_1$ and $R_2$ as aroyl groups are e.g. benzoyl, 1-or 2-naphthoyl, but are preferably benzoyl which is substituted by halogen atoms such as chlorine or bromine atoms, or by $C_1$–$C_{12}$alkyl, $C_1$–$C_{12}$alkoxy, trifluoromethyl or nitro groups.

$R_1$ and $R_2$ as alkanoyl groups are e.g. $C_2$–$C_5$alkanoyl groups such as methylcarbonyl, ethylcarbonyl, n-propylcarbonyl and tert-butylcarbonyl groups.

Alkyl radicals $R_3$, $R_4$ and $R_5$ are the same alkyl groups as previously mentioned in connection with the definition of A, B, $R_1$ and $R_2$.

$R_3$, $R_4$ and $R_5$ as aryl are e.g. phenyl or naphthyl, preferably phenyl or phenyl which is substituted by halogen such as chlorine or bromine, $C_1$–$C_6$alkyl or $C_1$–$C_6$alkoxy.

—$N(R_3)(R_4)$ as a 5- or 6-membered heterocyclic radical is e.g. a morpholine or piperidine radical.

Representative examples of $N^+H(R_3)(R_4)(R_5)$ are: $N^+H_4$, $N^+H_3CH_3$, $N^+H_2(CH_3)_2$, $N^+H_3C_2H_5$, $N^+H_2(C_2H_5)_2$, $N^+H_3C_3H_7$-iso, $N^+H_3$-cyclohexyl, $N^+H_2$-(cyclohexyl)$_2$, $N^+H_2(CH_3)(C_6H_5)$, $N^+H_3C_6H_5$, $N^+H_3$-para-toluidine and $N^+H_3$-benzyl.

Representative examples of —$N(R_4)(R_5)$ are: —$NHCH_3$, —$N(CH_3)_2$, —$NHC_2H_5$, —$N(C_2H_5)_2$, —NH-cyclohexyl, —$NHC_6H_5$ and —$NHCH_2C_6H_5$.

The groups of formula

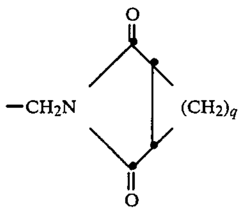

are derived from aliphatic dicarboxylic acids, e.g. from succinic acid or 1,2-cyclobutanedicarboxylic acid.

L as a group of formula $$\frac{M^{+n}}{n}$$

is e.g. an alkali metal cation or alkaline earth metal cation or a transition metal cation, preferably $Na^+$, $K^+$, $Mg^{2+}$, $Ca^{2+}$, $Sr^{2+}$, $Ba^{2+}$, $Mn^{2+}$, $Zn^{2+}$, $Cu^{2+}$, $Ni^{2+}$, $Cd^{2+}$, $Co^{3+}$, $Al^{3+}$ and $Cr^{3+}$.

Component (b) of the composition of formula I may contain up to 4 groups —$SO_3L$, —$CO_2L$, —$PO_3L$, —$N(R_4)(R_5)$,

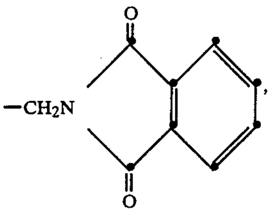

,

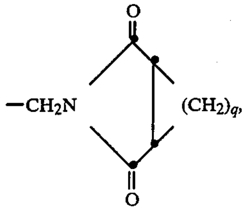

,

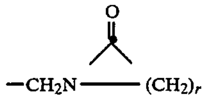

or —NHCOR, but preferably contains one of said groups per radical A, B, $R_1$ and $R_2$. Groups of formulae —$SO_3L$ and —$N(R_4)(R_5)$ are preferred, with the group of formula —$SO_3L$ being particularly preferred.

Particularly interesting compositions are those comprising (a) a pyrrolopyrrole of formula II (II)

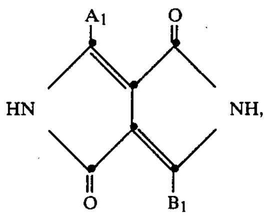

wherein $A_1$ and $B_1$ are each independently of the other aryl radicals, and (b) a pyrrolopyrrole of formula III (III)

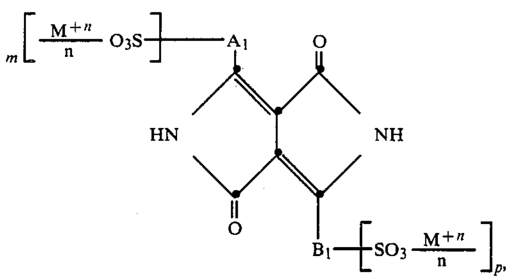

wherein $A_1$ and $B_1$ are as defined above, M is an alkali metal cation, an alkaline earth metal cation or a transition metal cation, n is 1, 2 or 3, and m and p are each independently of the other 0, 1, 2, 3 or 4, with the sum of m+p being at least 1.

The preferred meaning of $A_1$ and $B_1$ as aryl in formulae II and III above is phenyl or phenyl which is substituted by water-insolubilising substituents. Examples of suitable water-insolubilising substituents are the same as those previously indicated above in the definition of the radicals A and B.

Especially preferred compositions contain a pyrrolopyrrole of formula II and a pyrrolopyrrole of formula III, wherein $A_1$ and $B_1$ are phenyl or p-chlorophenyl and m and p are 0 or 1, with the sum of m+p being at least 1, n is 1 or 2 and M is $Na^+$, $K^+$, $Mg^{2+}$, $Ca^{2+}$, $Sr^{2+}$ or $Ba^{2+}$, and the sulfonic acid radical in the phenyl nucleus is para to the diketopyrrolopyrrole nucleus.

The compositions of this invention can be prepared by mixing the individual pyrrolopyrrole components (a) and (b) in the desired ratio or also by partial sulfonation, alkylation or acylation of the pyrrolopyrrole component (a).

Component (b) of the compositions of this invention containing at least one $—SO_3L$ group can be prepared by methods which are known per se, for example by sulfonating the pyrrolopyrrole component (a) with oleum, sulfuric acid, liquid sulfur trioxide or chlorosulfonic acid, with the proviso that at least one of the groups A, B, $R_1$, $R_2$, $A_1$ and $B_1$ must have a site that can be sulfonated. The concentration of sulfonating agent and the reaction conditions are closely connected with the number of sulfonic acid groups which it is desired to introduce into the pyrrolopyrrole molecule. The products so obtained are subsequently converted into the corresponding metal or amine salt derivatives with a suitable metal salt, e.g. an acetate, carbonate, chloride, nitrate or sulfate, or with an amine.

The pyrrolopyrroles of component (a) of the composition of this invention are known compounds and can be obtained e.g. in accordance with U.S. Pat. No. 4,579,949.

Component (b) of the compositions of this invention containing at least one $—CO_2L$ or $—PO_3(L)_2$ group can be obtained e.g. from a corresponding pyrrolopyrrole derivative which contains carboxyl, carbonitrile, esterified carboxyl, phosphonic acid or phosphonic acid ester groups, the nitrile or ester groups of which derivatives can be converted into the free acid or acids by conventional saponification methods. These acids can then be converted into their metal or amine salts by reaction with the eligible metal salts or amines. The required starting materials can be prepared e.g. from a nitrile derivative containing an additional nitrile, carboxylic acid, esterified carboxyl, phosophonic acid or phosphonic acid ester group by reaction with a succinate in the presence of a strong base in accordance with European patent application No. EP-A-0,094,911.

Component (b) containing carboxamide or dicarboximide groups can in turn be obtained by reacting the pyrrolopyrrole component (a) with formaldehyde and a carboxamide or dicarboximide or with hydroxymethylene-N-carboxamide or hydroxymethylene-N-dicarboximide.

The ratios of the components of the compositions of this invention may vary freely. Preferred ratios, however, are from 0.1 to 25% by weight of component (b) and 99.9 to 75% by weight of component (a).

The compositions of the invention can be used as pigments for colouring high molecular organic material.

Depending on the utility, the compositions of this invention can be used in a more opaque or more transparent pigmentary form.

If it is desired to obtain a more opaque pigment form, then it is usually expedient to effect a thermal aftertreatment in water or an organic solvent, under normal or elevated pressure. It is preferred to use organic solvents such as benzenes which are substituted by halogen atoms, alkyl or nitro groups, for example xylenes, chlorobenzene, o-dichlorobenzene or nitrobenzene, as well as pyridine bases such as pyridine, picoline or quinoline, and also ketones such as cyclohexanone, alcohols such as isopropanol, butanols or pentanols, ethers such as ethylene glycol monomethyl or monoethyl ether, amides such as dimethylformamide or N-methylpyrrolidone, as well as dimethylsulfoxide or sulfolane. The aftertreatment can also be carried out in water, under normal or elevated pressure, in the presence of organic solvents and/or with the addition of surfactants.

Examples of high molecular organic materials which may be coloured with the compositions of this invention are cellulose ethers and esters such as ethyl cellulose, nitrocellulose, cellulose acetate, cellulose butyrate, natural resins or synthetic resins such as polymerisation resins or condensation resins, for example aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyesters, rubber, casein, silicone and silicone resins, singly or in mixtures.

The above high molecular organic compounds may be singly or as mixtures in the form of plastics, melts or of spinning solutions, varnishes, paints or printing inks. Depending on the end use, it is advantageous to use the compositions as toners or in the form of preparations. The compositions obtained by the process of the invention are preferably employed in an amount of 0.01 to 30% by weight, preferably 0.1 to 10% by weight, based on the high molecular organic material to be pigmented.

The pigmenting of the high molecular organic compounds with the compositions of the invention is carried out for example by incorporating such a composition, optionally in the form of a masterbatch, into the substrates using roll mills, mixing or grinding machines. The pigmented material is then brought into the desired final form by methods which are known per se, for example calendering, moulding, extruding, coating, spinning, casting or by injection moulding. It is often desirable to incorporate plasticisers into the high molecular compounds before processing in order to produce non-brittle mouldings or to diminish their brittleness. Suitable plasticisers are for example esters of phosphoric acid, phthalic acid or sebacic acid. The plasticisers may be incorporated before or after working the pigment into the polymers. To obtain different shades, it is also possible to add fillers or other chromophoric components such as white, coloured or black pigments, in any amount, to the high molecular organic compounds, in addition to the compositions obtained by the process of this invention.

For pigmenting varnishes and printing inks, the high molecular organic materials and the compositions obtained by the process of the invention, together with optional additives such as fillers, other pigments, siccatives or plasticisers, are finely dispersed or dissolved in a common organic solvent or mixture of solvents. The procedure may be such that the individual components by themselves, or also several jointly, are dispersed or dissolved in the solvent and subsequently all the components are mixed.

The colourations obtained, for example in plastics, filaments, varnishes or prints, have good allround fastness properties such as good dispersibility, high tinting strength, good fastness to overspraying, migration, heat, light, and weathering, as well as good gloss.

In addition, compared with the unsulfonated, non-carboxylated, non-phosphonated or non-N-imidomethylated pyrrolopyrroles, the compositions of this invention have an enhanced rheology, especially in varnishes and printing inks as well as improved heat resistance and distortion resistance in application.

The present invention further relates to novel compounds of formula IV

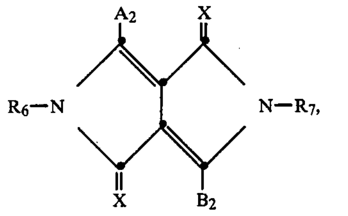
(IV)

containing at least one group of the formulae $—SO_3L$, $—CO_2L$, $—PO_3(L)_2$,

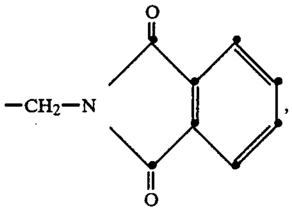
,
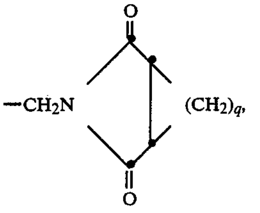

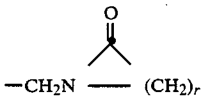

or —NHCOR, wherein $A_2$ and $B_2$ are identical or different alkyl, aralkyl, aryl or heterocyclic aromatic radicals, $R_6$ and $R_7$ are hydrogen atoms, unsubstituted or substituted alkyl radicals, and also alkenyl, alkynyl, aralkyl, cycloalkyl, benzyl, carbamoyl, alkylcarbamoyl, arylcarbamoyl, alkoxycarbonyl, aryl, alkanoyl or aroyl groups, and X is an —O— or —S— atom, L is —H, a group of formula $$\frac{M^{+n}}{n}$$

or $N^+H(R_8)(R_9)(R_{10})$, M is a monovalent, divalent or trivalent metal cation, n is 1, 2 or 3, $R_8$, $R_9$ and $R_{10}$ are each independently —H or alkyl, aralkyl, $C_5$–$C_6$cycloalkyl or aryl radicals, or $R_9$ and $R_{10}$, together with the nitrogen atom to which they are attached, form a 5- or 6-membered heterocyclic radical, q is an integer from 0 to 4, r is an integer from 3 to 5 and R is aryl or $C_1$–$C_4$alkyl, with the proviso that L may not be a sodium cation if the compounds of formula IV contain a $—SO_3L$ group.

The definitions and preferred meanings of the various symbols $A_2$, $B_2$, R, $R_6$ to $R_{10}$, X, L, M, n, q and r are the same as previously indicated for the corresponding groups A, B, R, $R_1$ to $R_5$, X, L, M, n, q and r.

Particularly preferred compounds are those of formula V

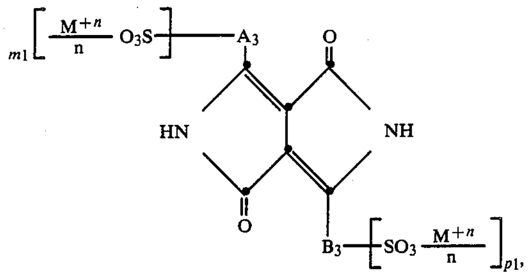
(V)

wherein $A_3$ and $B_3$ are phenyl or naphthyl and $m_1$ and $p_1$ are 0 or 1, with the sum of $m_1+p_1$ being at least 1, and n is 1, 2 or 3, and M is an alkaline earth metal cation or a transition metal cation, $Li^+$ or $K^+$.

The most preferred compounds are those of formula V, wherein $A_3$ and $B_3$ are phenyl and $m_1$ and $p_1$ are 0 or 1, with the sum of $m_1+p_1$ being at least 1, n is 1 or 2, and M is $K^+$, $Ca^{2+}$, $Mg^{2+}$, $Sr^{2+}$, $Ba^{2+}$, $Zn^{2+}$ or $Cd^{2+}$.

The compounds of formulae IV and V can be obtained by the same preparatory methods which have already been described for the preparation of the components (b) of the compositions of this invention.

The compounds of formula IV and V are useful novel intermediates which can be used e.g. for synthesising further pyrrolopyrroles, for example for the preparation of acid amides and acid ester derivatives from the corresponding sulfonic acid, carboxylic acid or phosphonic acid derivatives.

The compounds of formulae IV and V can also be used as pigments for colouring the high molecular organic materials referred to above. For this utility they can be used as crude products or after an appropriate conditioning/aftertreatment, for example as described above for the compositions of this invention.

In the following Examples percentages are by weight.

EXAMPLE 1

With stirring, 6 g of 1,4-diketo-3,6-diphenylpyrrolo[3,4-c]pyrrole are added over 10 minutes at 10°–15° C. to 78 g of fuming sulfuric acid (25% $SO_3$). The resultant mixture is stirred for 3 hours at 15°–20° C. and then poured onto 800 g of ice. After standing for 16 hours at 20° C., the resultant suspension is filtered and the dark red product is washed 3 times with a small amount of water and then dissolved at 80° C. in about 700 g of water with the addition of ammonia solution. To the cherry red solution so obtained are added 45 g of ammonium chloride at 80° C. with stirring, and stirring is continued for 30 minutes at 80° C. The precipitate is isolated by filtration at 60° C., washed with a 2% solution of ammonium chloride and dried at 100° C., affording 7.6 g of a dark red product which consists substantially of the ammonium salt of 1,4-diketo-3,6-phenylpyrrolo[3,4-c]pyrrole-4'-monosulfonic acid. This product dissolves in cold water to form a cherry red solution. When this aqueous solution is boiled, the colour turns to orange red. The original colour returns when the hot solution cools.

EXAMPLE 2

10 g of 1,4-diketo-3,6-diphenylpyrrolo[3,4-c]pyrrole are added over 10 minutes at 5°–10° C. to 150 g of fuming sulfuric acid (12.5% $SO_3$). The resultant mixture is stirred for 16 hours at 20° C. and then poured onto 700 g of ice. The resultant solution is bulked with water to 1100 g and 60 g of sodium chloride are added at 75° C., with stirring. The colour of the resultant suspension turns in a short time from orange to red. A spotting test runs colourless. After stirring for ½ hour at 70°-75° C., the precipitate is isolated by filtration and washed with a 5% solution of sodium chloride until neutral. After washing twice with water, the moist product is suspended in water. To the suspension, which is made up to 600 g, is added a solution of 25 g of barium chloride ($BaCl_2.2H_2O$) in 100 g of water at 90°-95° C. over 20 minutes and the mixture is kept at the boil for 1 hour. The precipitate is isolated by filtration, washed 6 times with cold water and then freeze dried, affording 19.4 g of a dark red product which consists substantially of the barium salt of 1,4-diketo-3,6-diphenylpyrrolo[3,4-c]pyrrole-4',4''-disulfonic acid. Water determination (weight loss at 130° C.): 3.2%.

| | | | |
|---|---|---|---|
| Corrected analysis: found: | Na 0.51% | theory: | — |
| | Ba 22.0% | | 23.53% |
| | S 11.0% | | 10.98%. |

The product colours varnishes and plastics in lightfast red shades. It has excellent heat resistance in HDPE.

EXAMPLE 3

Following the procedure of Example 2, the clacium salt of 1,4-diketo-3,6-diphenylpyrrolo[3,4-c]pyrrole-4',4''-disulfonic acid is obtained.

Yield: 16.7 g.

Analysis: Water expelled at 150° C., weight loss: 6.2%. Ca (corr.) found: 7.94% theory: 8.42%. S (corr.) found: 12.42% theory: 13.18%.

The product colours varnishes and PVC in lightfast red shades and with very good fastness to migration.

EXAMPLE 4

70 g of 1,4-diketo-3,6-diphenylpyrrolo[3,4-c]pyrrole are added over 20 minutes at 5°-12° C. to 1050 g of fuming sulfuric acid (12.5% $SO_3$). The resultant mixture is stirred for 16 hours at 20° C. and then poured onto ice. Final volume: 9000 ml. To the resultant solution are added 450 g of sodium chloride, whereupon an orange precipitate initially forms. The suspension is then heated to 75° C., whereupon the colour of the suspension turns red. After stirring for 30 minutes at 75° C., the suspension is filtered and the filter cake is washed 3 times with water. The moist product is suspended in water and the suspension is bulked with water to 1500 g and adjusted to pH at 75° C. with a solution of sodium hydroxide, with stirring. After stirring for ½ hour, the suspension is filtered once more and the residue is washed twice with cold water and dried under vacuum at 120° C., affording 113 g of the sodium salt of the 1,4-diketo-3,6-diphenylpyrrolo[3,4-c]pyrrole-4',4''-disulfonic acid in the form of a dark red product.

EXAMPLE 5

With stirring, 20 g of 1,4-diketo-3,6-diphenylpyrrolo[3,4-c]pyrrole are added over 10 minutes at 5°-10° C. to 300 g of fuming sulfuric acid (12.5% $SO_3$). The resultant mixture is stirred for 19 hours at 20° C. and then poured onto ice, and the mixture is bulked to 2000 g with water. With stirring, a solution of 8.05 g of hexamethylenediamine in 200 g of water and 8.3 g of formic acid are added dropwise at 20° C. over 20 minutes. After initial turbidity, a precipitate begins to form towards the end of the dropwise addition. After stirring for 5 hours at 20°-25° C., the suspension is filtered and the filter cake is washed with cold water until neutral. The filter cake is then dried at 90° C. under vacuum, affording 33.5 g of the hexamethylenediamine salt of 1,4-diketo-3,6-diphenylpyrrolo[3,4-c]pyrrole-4',4''-disulfonic acid.

Analysis: theory: for $C_{24}H_{28}N_4O_8S_2$: C 51.05 H 5.00 N 9.92 S 11.36%; found: C 50.18 H 5.12 N 9.65 S 11.23%.

The di-o-tolylguanidine, dicyclohexylamine, $C_{12}H_{25}$ and $C_{18}H_{36}/C_{22}H_{45}$-amine salts of 1,4-diketo-3,6-diphenylpyrrolo[3,4-c]pyrrole-4',4''-disulfonic acid can also be prepared in corresponding manner.

EXAMPLE 6

With stirring, 20 g of 1,4-diketo-3,6-diphenylpyrrolo[3,4-c]pyrrole are added at 5°-10° C. to 300 g of fuming sulfuric acid (12.5% $SO_3$). The resultant mixture is stirred for 19 hours at 20° C. and then poured onto ice, and the mixture is bulked to 2000 g with water. A solution of 14.85 g of 4-toluidine in 70 g of 100% acetic acid is then added dropwise over 10 minutes to the above solution. A precipitate forms during the addition of the 4-toluidine solution. After stirring for 4 hours at 20° C., the orange red precipitate is isolated by filtration, washed with cold water until neutral and dried at 90° C. under vacuum, affording 42.9 g of the 4-toluidine salt of 1,4-diketo-3,6-diphenylpyrrolo[3,4-c]pyrrole-4',4''-disulfonic acid.

Analysis: theory: C 57.99 H 4.56 N 8.45 S 9.68%; found: C 57.34 H 4.62 N 8.27 S 9.64%.

EXAMPLE 7

With stirring, 5.1 g of the sodium salt of 1,4-diketo-3,6-diphenylpyrrolo[3,4-c]pyrrole-4',4''-disulfonic acid obtained in Example 4, 150 g of water and 5 g of crystallised magnesium sulfate are heated for 17 hours to the boil. The resultant white suspension is filtered, the residue is washed 5 times with hot water and vacuum dried at 110° C., affording 5 g of the corresponding magnesium salt in the form of a dark red product.

Analysis: Mg theory: 5.15%; Mg found (corr.): 4.49%; Na found (corr.): 0.5%; water theory: 9.3%.

The product colours varnishes and plastics in red shades of excellent fastness to light and migration and has very good resistance in HDPE.

The aluminium, zinc, cadmium, copper and nickel salts of 1,4-diketo-3,6-diphenylpyrrolo[3,4-c]pyrrole-4',4''-disulfonic acid are obtained in corresponding manner. These salts are also suitable for colouring varnishes and plastics and have good allround pigment properties and good heat resistance in HDPE.

EXAMPLE 8

20 g of 1,4-diketo-3,6-diphenylpyrrolo[3,4-c]pyrrole are added over 15 minutes at 5°-10° C. to 300 g of fuming sulfuric acid (12.5% $SO_3$). After stirring for ½ hour at 15°-20° C., 17 g of acetic anhydride are added dropwise over 20 minutes at 4°-8° C. The mixture is then stirred for 21 hours at 20° C. Orange crystals begin to precipitate 5 hours after addition. A suspension of compact crystals is obtained at the conclusion of the reaction. With cooling, 100 g of 100% acetic acid are added dropwise at 10°-20° C. over 1 hour, whereupon again a solution is obtained. The mixture is stirred for a further 24 hours at 20° C. and the resultant suspension is filtered through a glass frit and the residue is washed 3 times with 100% acetic acid. The product is suspended in 100% acetic acid, isolated by filtration once more, and washed 5 times with 100% acetic acid and vacuum dried, affording 29 g of a dark powder which corresponds to 1,4-diketo-3,6-diphenylpyrrolo[3,4-c]pyrrole-4',4"-disulfonic acid according to combustion analysis and NMR spectrum.

EXAMPLE 9

With stirring, 10 g of the free 1,4-diketo-3,6-diphenylpyrrolo[3,4-c]pyrrole-4',4"-disulfonic acid obtained in Example 8 are added at 20° C. to 105 g of chlorosulfonic acid. The resultant solution is cooled to 5° C., then 49 g of thionyl chloride are added dropwise over 10 minutes. The mixture is stirred for 3½ hours at 60° C. and then cooled to 10° C. The reaction mixture is then added, with stirring, to a mixture of 1200 g of ice and 200 g of sodium chloride. The precipitate is isolated by filtration, washed free from acid with a 10% solution of sodium chloride and dried at 70° C. under vacuum, affording 1,4-diketo-3,6-diphenylpyrrolo[3,4-c]pyrrole-4',4"-disulfonic acid chloride containing sodium chloride. The product is in the form of a dark red powder.

EXAMPLE 10

With stirring, 14.5 g of 1,4-diketo-3,6-diphenylpyrrolo[3,4-c]pyrrole are added over 10 minutes at 0°-5° C. to 290 g of 96% sulfuric acid. After stirring for 1 hour, 290 g of sulfuric acid monohydrate are added, whereupon a solution forms. Then 18.1 g of N-hydroxymethylphthalimide are added at 5° C. over 15 minutes. The temperature is raised to 14° C. over 3 hours and stirring is continued for 16 hours at 15°-20° C. The mixture is then poured into 3000 g of ice-water, the brownish yellow precipitate is isolated by filtration, washed free from acid with water and dried at 80° C., affording 29.9 g of a brownish yellow crude product. For purification, the pulverised crude product is stirred in 300 ml of ethanol for 1 hour at boiling temperature, the precipitate is isolated hot by filtration, washed with ethanol and dried at 60° C. The brownish yellow product so obtained consists of a mixture of compounds of the formula

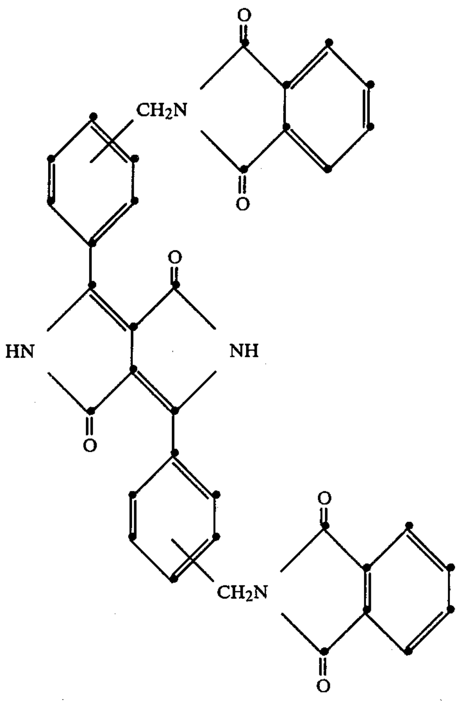

EXAMPLE 11A

A 350 ml sulfonating flask equipped with propeller stirrer is charged with 4.83 g of sodium, 0.1 g of sodium bis(2-ethylhexyl)sulfosuccinate (as emulsifier) and 85 ml of tert-amyl alcohol, and the mixture is heated to 95°-102° C. With efficient stirring, the fused metal is dissolved in the alcohol. The solution is cooled to c. 90° C. To this solution are added 15.0 g of dried 3-cyanobenzoic acid and then 11.8 g of distilled di-tert-butylsuccinate. The mixture is heated to weak reflux (c. 95° C. to a maximum temperature of 101° C.) and further stirred at this temperature for 6 hours. The reaction mixture is then cooled to 35° C., diluted with 85 ml of methanol, slowly neutralised with 13 g of glacial acetic acid, diluted with a further 30 ml of methanol, refluxed for 2 hours and filtered at 50° C. The product is washed with methanol, then with acetone and finally with dilute hydrochloric acid (0.1N) and dried in a vacuum oven at 80° C., affording an orange product of formula

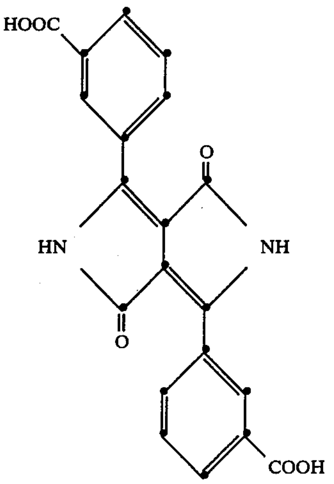

EXAMPLE 11B

A 200 ml sulfonating flask equipped with propeller stirrer is charged, in succession, with 8.7 g of potassium tert-butylate, 55 ml of tert-butanol, 9.65 g of isopropyl 3-cyanobenzoate (distilled), and 5.6 g of distilled diisopropyl succinate. The reaction mixture is heated to reflux (c. 85° C.) and kept at reflux for 5 hours. The reaction mixture is then cooled to 50° C. and, after the dropwise addition of 55 ml of methanol, slowly neutralised with a mixture of 6.9 g of glacial acetic acid and 5 ml of methanol, and the whole batch is transferred to a glass beaker containing 200 ml of methanol and 50 ml of water. After brief stirring, the product is isolated by filtration and the residue is washed with aqueous methanol (1:1) and dried at 80° C. in a vacuum oven, affording 4.75 g of a crude product (=41.3% of theory).

3.70 g of the above crude product (1,4-diketo-3,6-diphenylpyrrolo[3,4-c]pyrrole-3',3''-isopropoxycarbonyl) are added to a mixture of 45 ml of dimethylsulfoxide and 15 ml of water and then a solution of 4.67 g of 30% sodium hydroxide solution and 5 ml of water are added. After stirring for 2½ hours, the pH is c. 12. The reaction mixture is then adjusted to pH 1.5 by addition of concentrated hydrochloric acid (diluted with water 1:1) and refluxed for 3 hours. The reaction mixture is then cooled to 80° C., the product is isolated by filtration and washed in succession with methanol, acetone and warm water, and dried at 80° C. in a vacuum oven, affording the compound of Example 11A of the indicated structure in the form of an orange powder.

EXAMPLE 11C 0.94 g of the compound of Example 11B is suspended in a 1:1 mixture of dimethylsulfoxide/water (60 ml) and 1.47 g of 30% sodium hydroxide solution are added. The resultant suspension is stirred for 2 hours at 60° C., then 0.5 ml of glacial acetic acid are added to adjust the pH to 8.5. Then 0.44 g of calcium acetate are added and the reaction mixture is refluxed for a further 3 hours. After cooling to 60° C., the suspension is diluted with 120 ml of water, stirred for 30 minutes at this temperature and filtered. The pigment salt is washed with hot water and dried overnight at 80° C. in a vacuum oven, affording an orange powder of the following structure

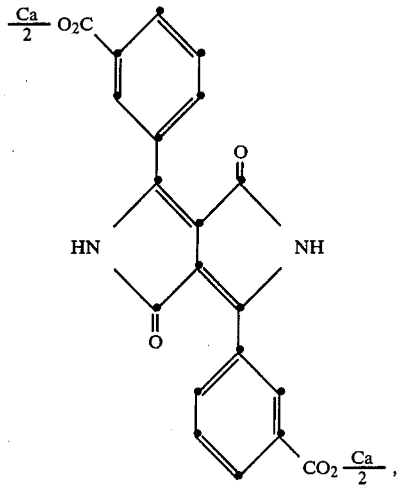

which has very good pigment properties on application.

EXAMPLE 11D

The procedure of Example 11C is repeated, using 0.607 g of zinc acetate.$2H_2O$ instead of calcium acetate, to give the compound of formula

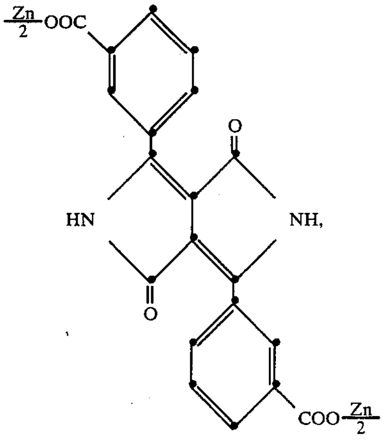

which colours PVC orange.

EXAMPLE 12A 7.0 g of the compound prepared in Example 4 are dissolved in 60 g of 98% sulfuric acid and the solution is diluted with water to a volume of 2 liters. Then 140 g of the pigment prepared in accordance with Example 6 of U.S. Pat. No. 4,579,949 are added as moist filter cake, the batch is bulked with water to 4 l and stirred for 4 hours at room temperature. The mixture is then heated to 75° C., 100 g of sodium chloride are added over 30 minutes and, stirring is continued for 30 minutes at this temperature. The suspension is then cooled to room temperature and filtered. The filter residue is washed first with 2 l of a 2% solution of sodium chloride and then with water, affording 480 g of a water-containing mixture which is further processed in accordance with Examples 12B to 12E.

EXAMPLE 12B 120 g of the water-containing mixture obtained in Example 12A are dried overnight at c. 80° C. under vacuum, affording 36 g of a product mixture consisting of the compounds of formulae

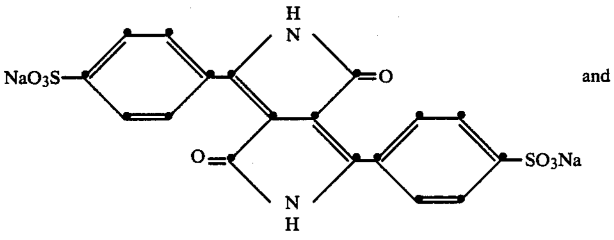

and

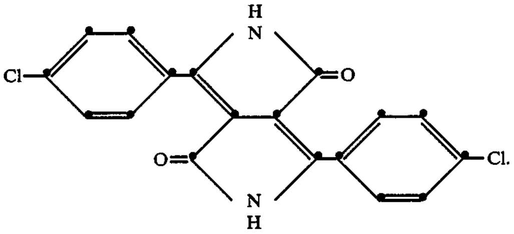

EXAMPLE 12C 120 g of the water-containing mixture obtained in Example 12A are dispersed in water to a volume of 1500 ml and heated to 90°-95° C. Then 4.5 g of $BaCl_2.2H_2O$ are dissolved in a small amount of water and added dropwise to this dispersion over 30 minutes. The suspension is stirred for 1 hour at this temperature, then cooled to room temperature, filtered, and the filter product is washed with water and dried, affording 39.3 g of a mixture consisting of the compounds of formulae

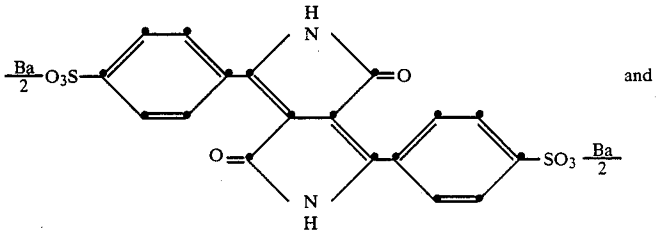

and

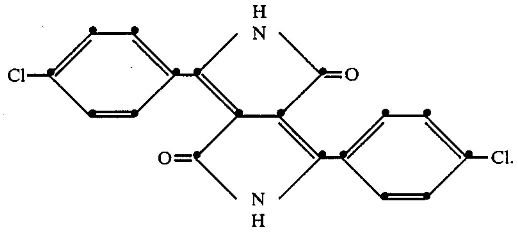

EXAMPLE 12D

The procedure of Example 12C is repeated, using 8 g of $Al_2(SO_4)_3.18H_2O$ instead of $BaCl_2.2H_2O$, to give 34.7 g of a mixture consisting of the compounds of formula

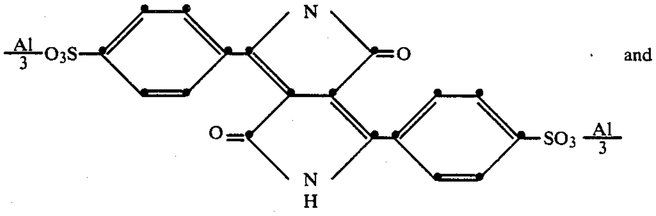

and

-continued

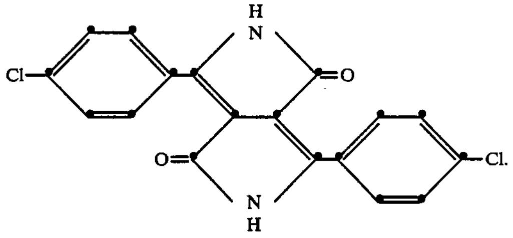

EXAMPLE 12E

The procedure of Example 12C is repeated, using 3 g of $MgSO_4$ instead of $BaCl_2.2H_2O$, to give 35.6 g of a mixture consisting of the compounds of formulae

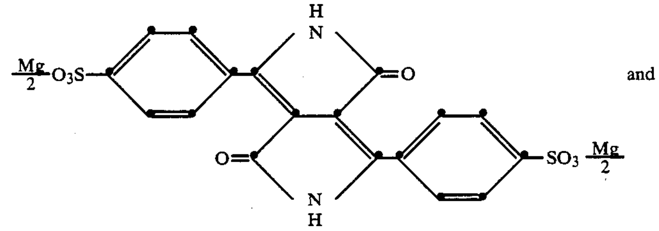

and

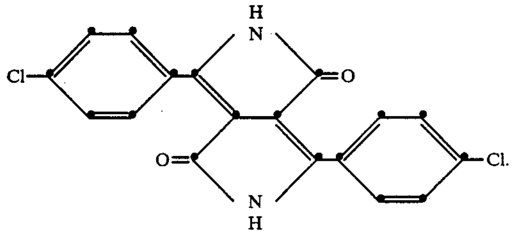

EXAMPLE 13

1.42 g of the pigment prepared in accordance with Example 12 of U.S. Pat. No. 4,579,949 are dissolved in 300 ml of 98% $H_2SO_4$ and the solution is diluted with water to a volume of 1500 ml. The resultant suspension is refluxed, and then 33.2 g of the compound prepared in accordance with Example 6 of U.S. Pat. No. 4,579,949 are added in portions as moist filter cake to the violet solution and the batch is stirred for 4 hours. With stirring, the batch is cooled to 60° C., filtered, and the filter cake is washed with water until neutral and vacuum dried at 80° C. overnight, affording 32.7 g of a mixture consisting of the compounds of formulae

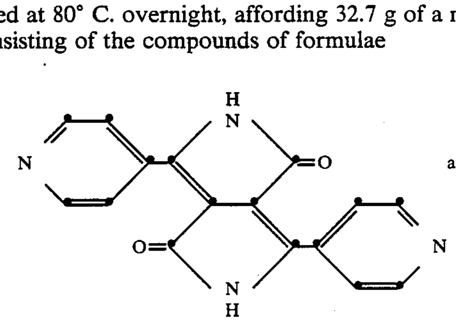

and

-continued

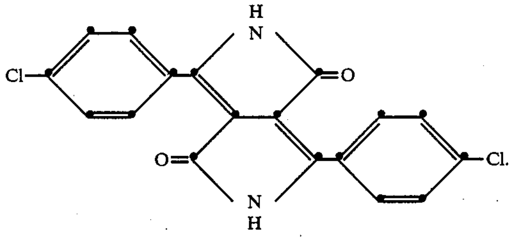

EXAMPLE 14

1.84 g of the compound prepared in Example 11A are dissolved in 300 ml of water and 15 ml of 30% sodium hydroxide solution. Then 33 g of the compound prepared in accordance with Example 6 of U.S. Pat. No. 4,579,949 are added as moist filter cake. The resultant suspension is stirred for 3 hours, heated to 75° C., and then a solution of 4.5 g of $BaCl_2.2H_2O$ in 50 ml of water is added at this temperature over 30 minutes and the batch is stirred for 2 hours. After cooling to room temperature, the suspension is filtered and the residue is washed with water until neutral and dried at 80° C. under vacuum overnight, affording 35.3 g of a mixture of the compounds of formulae

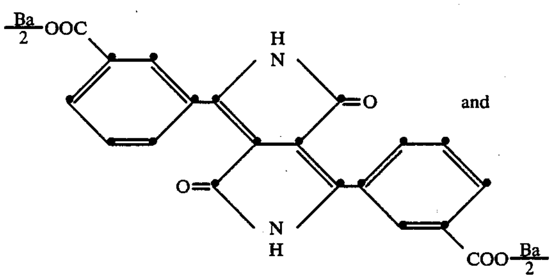

and

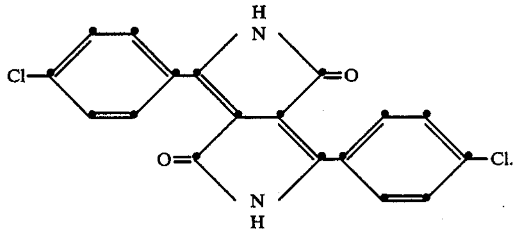

EXAMPLE 15

By measuring under strictly comparable conditions the viscosity of a 6% alkyd/melamine varnish mill base formulation of the mixture obtained in Example 12B by means of a rotary viscosimeter (available from Brookfield Engineering Laboratories, Stoughton, Mass., U.S.A.) lower viscosities at different spindle speeds (at 1.5, 6, 30 and 60 rpm) are obtained for the mixture obtained in Example 12B than those of the untreated pigment (Example 6 of U.S. Pat. No. 4,579,949) and thus better rheological properties in application.

EXAMPLE 16

A 100 ml sulfonating flask equipped with propeller stirrer is charged, under argon, in succession with 6.94 g of potassium tert-butylate, 35 ml of tert-butanol, 10.63 g of crude diethyl 4-cyanophosphonate and 4.09 g of diisopropyl succinate. The reaction mixture is heated to reflux (78°-81° C.) amd kept at this temperature for 4.5 hours. The reaction mixture is then cooled to 50° C., poured into a 50 ml dropping funnel and added dropwise over 10 minutes to 100 ml of ice-water. After brief stirring, 22 ml of concentrated hydrochloric acid (c. 18%) are added to the suspension until the pH is 1.5. The resultant suspension is then stirred at room temperature and filtered. The filter cake is washed with hot water and dried at 80° C. in a vacuum oven, affording 3.11 g of a product that consists substantially of a mixture of the compounds of formula

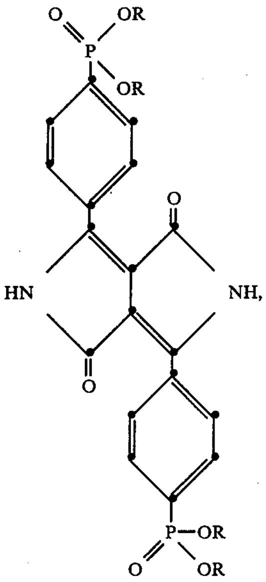

wherein R is ethyl, isopropyl and tert-butyl. This mixture can be converted into the corresponding phosphoric acid monoester derivatives of formula

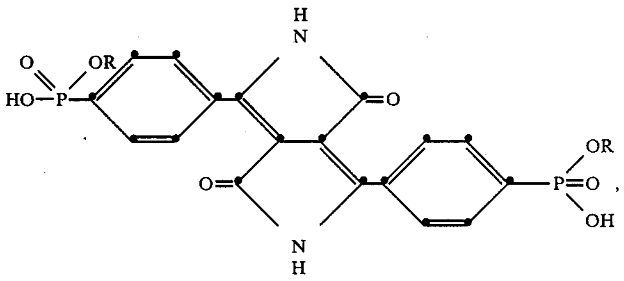

wherein R is as defined above, in a 1:1 mixture of water/dimethylformamide.

EXAMPLE 17

To a mixture of 40 g of fuming sulfuric acid (25% $SO_3$) and 40 g of sulfuric acid monohydrate are added at 2°-5° C. over 10 minutes 5.0 g of 1,4-diketo-3-phenyl-6-(4'-chlorophenyl)pyrrolo[3,4-c]pyrrole which has been prepared in accordance with Example 6 of European patent application No. 0,184,982. After stirring for ½ hour at 5° C., the mixture is further stirred for 17 hours at 20° C. The mixture is then poured into ice-water. The weight of the mixture is 420 g. To this mixture are added 30 g of sodium chloride at 70°-75° C. and stirring is continued for 1 hour at the same temperature. After cooling to 20° C., the precipitate is isolated by filtration, washed free from acid with 5% sodium chloride solution and dried at 120° C., affording (allowing for the content of sodium chloride) 6.4 g of the sodium salt of the monosulfonic acid of 1,4-diketo-3-phenyl-6-(4'-chlorophenyl)pyrrol[3,4-c]pyrrole of formula

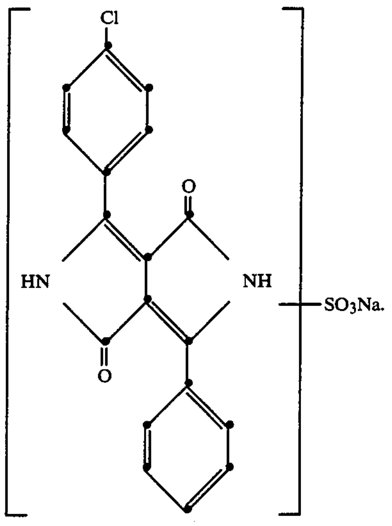

This product can be processed in the same manner as in Examples 12A/12B to pigment mixtures which enhance the rheological properties of varnishes.

EXAMPLE 18

To a mixture of 40 g of fuming sulfuric acid (25% $SO_3$) and 40 g of sulfuric acid monohydrate are added at 2°-5° C. over 10 minutes 5.0 g of 1,4-diketo-3-phenyl-6-(4'-methylphenyl)pyrrolo[3,4-c]pyrrole which has been prepared in accordance with Example 6 of European patent application No. 0,184,982 starting from 4-methylbenzonitrile instead of 4-chlorobenzonitrile. The mixture is stirred for 17 hours at 20° C. and then poured into ice-water. The weight of the mixture is 440 g. To this mixture are added 40 g of sodium chloride at 70°-75° C. over 30 minutes and stirring is continued for 1 hour at the same temperature. After cooling the suspension to 20° C., the precipitate is isolated by filtration, washed free from acid with 10% sodium chloride solution and dried at 120° C., affording (allowing for the content of sodium chloride) 8.5 g of the disodium salt of the disulfonic acid of 1,4-diketo-3-phenyl-6-(4'-chlorophenyl)-pyrrolo[3,4-c]pyrrole of formula

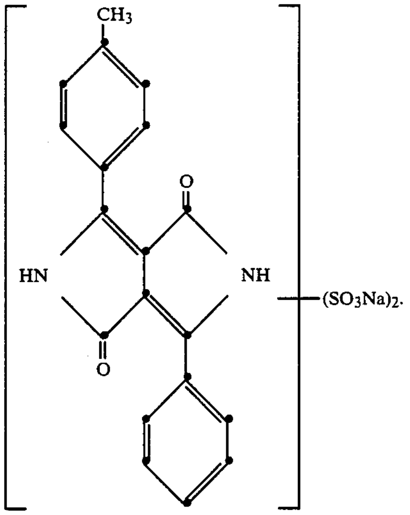

This product can be processed in the same manner as in Examples 12A/12B to pigment mixtures which enhance the rheological properties of varnishes.

EXAMPLE 19

40 g of fuming sulfuric acid (25% $SO_3$) are mixed with 40 g of sulfuric acid monohydrate and the mixture is cooled to 2°-5° C. With stirring, 5.0 g of 1,4-diketo-3,6-di-(biphenyl)pyrrolo[3,4-c]pyrrole, which has been prepared in accordance with Example 38 of U.S. Pat. No. 4,579,949, starting from p-phenylbenzonitrile instead of isophthalonitrile, are added to the above mixture. After stirring for 18 hours at 20° C., the mixture is then poured into ice-water. The weight of the mixture is 470 g. To this mixture are added 20 g of sodium chloride at 70°-75° C. After stirring for 1 hour at 70°-75° C., the precipitate is isolated by filtration at 20° C., washed free from acid with 4% sodium chloride solution and dried at 120° C., affording (allowing for the content of sodium chloride) 6.3 g of the disodium salt of 1,4-diketo-3,6-di-(biphenyl)pyrrolo[3,4-c]pyrrole disulfonic acid of formula

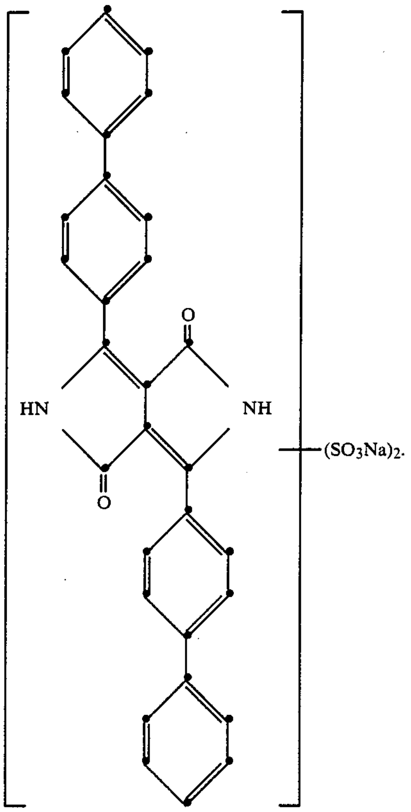

This product can be processed in the same manner as in Examples 12A/12B to pigment mixtures which enhance the rheological properties of varnishes.

EXAMPLE 20

The procedure of Example 19 is repeated, replacing the mixture (fuming sulfuric acid and sulfuric acid monohydrate) containing 12.5% $SO_3$ by 80 g of sulfuric acid monohydrate, to give (allowing for the sodium chloride content) 6.6 g of the disodium salt of 1,4-diketo-3,6-di-(biphenyl)pyrrolo[3,4-c]pyrroledisulfonic acid of the above formula.

What is claimed is:

1. A composition which is a mixture of pyrrolopyrrole pigments which comprises (a) 99.9 to 75% by weight of a pyrrolopyrrole pigment of formula I'

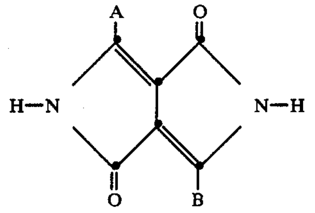

(I')

wherein A and B are identical or different phenyl groups or phenyl radicals which are substituted by water-insolubilizing substituents selected from the group consisting of halogen, $C_1$–$C_6$-alkyl, $C_1$–$C_4$-alkoxy, $C_1$–$C_6$-alkyl-mercapto, trifluoromethyl, cyano, dimethylamino, diethylamino, $C_2$–$C_6$-alkoxycarbonyl, acetylamino, carbamoyl or sulfamoyl, or A and B are 4-biphenylyl, naphthyl or pyridyl, and (b) 0.1 to 25% by weight of a modified pyrrolopyrrole pigment of formula I' which modified pigment additionally contains at least one group of formula $—SO_3L$, $—CO_2L$, $—PO_3(L)_2$, $—N(R_4)(R_5)$,

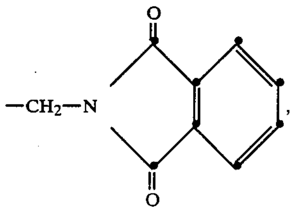, 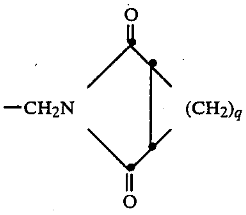 or

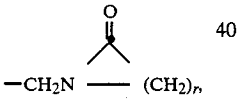

wherein L is —H, a group of formula $$\frac{M^{+n}}{n}$$

or $N^+H(R_3)(R_4)(R_5)$, M is a monovalent, divalent or trivalent metal cation, n is 1, 2 or 3, $R_3$, $R_4$ and $R_5$ are each independently —H or alkyl, benzyl, $C_5$–$C_6$cycloalkyl or phenyl radicals, or $R_4$ and $R_5$, together with the nitrogen atom to which they are attached, form a morpholine or piperidine radical, q is an integer from 0 to 4, and r is an integer from 3 to 5.

2. A composition according to claim 1, wherein A and B are identical and are phenyl radicals.

3. A composition according to claim 1, wherein L is —H or a group of formula $$\frac{M^{n+}}{n},$$

in which M is an alkali metal cation, an alkaline earth metal cation, or a transition metal cation selected from the group consisting of $Mn^{2+}$, $Zn^{2+}$, $Cu^{2+}$, $Ni^{2+}$, $Cd^{2+}$, $Co^{2+}$, $Al^{3+}$ and $Cr^{3+}$, and n is 1, 2 or 3.

4. A composition according to claim 1, comprising (a) a pyrrolopyrrole of formula II

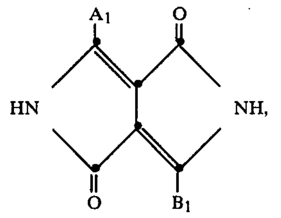

(II)

wherein $A_1$ and $B_1$ are each independently of the other phenyl or phenyl radicals which are substituted by water-insolubilizing substituents selected from the group consisting of halogen, $C_1$–$C_6$-alkyl, $C_1$–$C_4$-alkoxy, $C_1$–$C_6$-alkyl-mercapto, trifluoromethyl, cyano, dimethylamino, diethylamino, $C_2$–$C_6$-alkoxycarbonyl, acetyl amino, carbamoyl or sulfamoyl, and (b) a pyrrolopyrrole of formula III

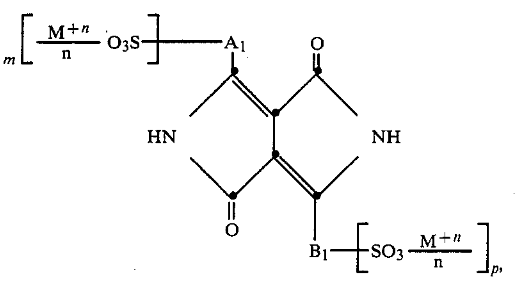

(III)

wherein $A_1$ and $B_1$ are as defined above, M is an alkali metal cation, an alkaline earth metal cation, or a transition metal cation selected from the group consisting of $Mn^{2+}$, $Zn^{2+}$, $Cu^{2+}$, $Ni^{2+}$, $Cd^{2+}$, $Co^{2+}$, $Al^{3+}$ and $Cr^{3+}$, n is 1, 2 or 3, and m and p are each independently of the other 0, 1, 2, 3 or 4, with the sum of m+p being at least 1.

5. A composition according to claim 4, wherein $A_1$ and $B_1$ are phenyl or p-chlorophenyl and m and p are 0 or 1, with the sum of m+p being at least 1, n is 1 or 2 and M is $Na^+$, $K^+$, $Mg^{2+}$, $Ca^{2+}$, $Sr^{2+}$ or $Ba^{2+}$, and the sulfonic acid radical in the phenyl nucleus is para to the diketopyrrolopyrrole nucleus.

* * * * *